United States Patent [19]

Pocalyko et al.

[11] Patent Number: 5,529,768
[45] Date of Patent: Jun. 25, 1996

[54] ALKYL ALDONOLACTONE ESTERS AND A PROCESS FOR THEIR MANUFACTURE

[75] Inventors: David J. Pocalyko, Lincoln Park; Angel J. Carchi, Hoboken; Bijan Harichian, South Orange; Robert C. Vermeer, Nutley, all of N.J.

[73] Assignee: Lever Brothers Company, New York, N.Y.

[21] Appl. No.: 437,495

[22] Filed: May 9, 1995

Related U.S. Application Data

[62] Division of Ser. No. 129,838, Sep. 30, 1993, Pat. No. 5,505,938.
[51] Int. Cl.$^6$ .................................................. A61K 7/00
[52] U.S. Cl. .................. 424/70.31; 252/DIG. 1; 252/DIG. 6; 252/DIG. 16
[58] Field of Search ............................. 424/70.31, 73; 252/89.1, 174, 174.17, 174.18, DIG. 5, DIG. 6, DIG. 13, DIG. 14, DIG. 16; 514/944, 975

[56] References Cited

U.S. PATENT DOCUMENTS 2,710,876  6/1955  Krebs et al. .
2,889,227  6/1959  Ofelt et al. .

FOREIGN PATENT DOCUMENTS 47-13190  4/1972  Japan .
89/01480  2/1989  WIPO .

OTHER PUBLICATIONS

Gallo et al., "Regioselective Acylations of Aldono–1,4–Lactones", Journal of Carbohydrate Chemistry, vol. 12, No. 7, pp. 841–851. (1993). Abstract Provided.

Copending application Ser. No. 08/129,838.

*Primary Examiner*—Melvyn I. Marquis
*Assistant Examiner*—Robert H. Harrison
*Attorney, Agent, or Firm*—James J. Farrell

[57] ABSTRACT

$C_{8-18}$ alkyl aldonolactone esters which have anionic and nonionic surfactant characteristics are disclosed. A process for preparing the esters enzymatically as well as personal product, cosmetic, detergent and oral hygiene compositions containing the compounds which take advantage of their dual surfactant quality, are also disclosed.

64 Claims, No Drawings

ALKYL ALDONOLACTONE ESTERS AND A PROCESS FOR THEIR MANUFACTURE

This is a Divisional application of Ser. No. 08/129,838 filed Sep. 30, 1993, now U.S. Pat. No. 5,505,938.

FIELD OF THE INVENTION

This invention relates to a new class of compounds which have both nonionic and anionic surfactant properties. In particular, this invention relates to a new process for the manufacture of long chained alkyl aldonolactone esters of the general formulas:

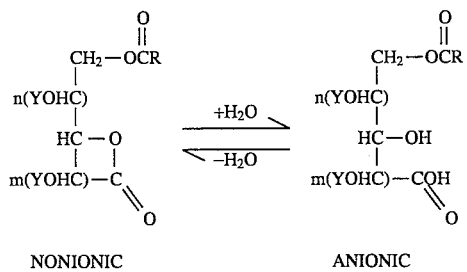

NONIONIC          ANIONIC wherein: n is from 0–3, m is from 2–3, Y is hydrogen or carbohydrate or ethoxylated or propoxylated carbohydrate and R is a straight saturated alkyl radical containing 10 to 14 carbon atoms or branched alkyl or alkenyl radical containing sufficient carbon atoms to render the compound surface active but at least six carbon atoms. The radical may also contain cylcoaliphatic or polyalkyloxyalkyl groups containing eight or more carbons.

BACKGROUND OF THE INVENTION

This invention is particularly addressed to the need for environmentally-friendly, mild, readily biodegradable, sugar-based surfactants that may be used in industrial applications, such as detergents, personal product, cosmetic, pharmaceutical, and dental compositions. This invention is also directed to the need of preparing alkyl aldonolactone esters regioselectively in high purity and good color.

The demand for mild, environmentally friendly surfactants has been steadily rising. In general, most detergent, personal product and dental compositions contain surfactants based on petrochemicals. Since these materials often have handling, storage and environmental hazards associated with them, it is desirable to use surfactants which are derived from agriculturally-grown materials such as carbohydrates. These naturally-occurring compounds represent a source of renewable raw materials that are readily available, inexpensive, biodegradable and optically pure.

DESCRIPTION OF RELATED ART

JP B-013910/72 to Yamanouchi Pharmaceutical Co. describes a process for the chemical esterification of an aldonolactone. Glucono-1,5-lactone is esterified with N,N-di-lower-alkylaminoacetic acid salt of the formula $HO_2CCH_2NR_1R_2 \cdot HX$ in the presence of a carbodiimide compound.

This process suffers from the distinct disadvantage of utilizing a carbodiimide compound to activate the acid for reaction with glucono-1,5-lactone. Carbodiimide compounds are usually not catalytic and therefore are used in stoichiometric amounts relative to the acid. The carbodiimide compounds are consumed during the reaction and consequently cannot be used in any subsequent reaction.

The process described by JP B 013910/72 results in the formation of a lactone ester containing a N,N-di-lower alkylaminoacetic acid functionality which is not surface active. For surface activity, an alkyl chain of 8 to 18 carbons in length is desirable. Alkyl fatty acids which are less expensive than N,N-di-alkyl-aminoacetic acid are also preferred.

U.S. Pat. No. 2,889,227 describes a process for the production of hydrogenated ascorbyl palmitate. Ascorbyl palmitate is hydrogenated using under 1600 lbs./sq. in. of pressure at 160° C. using Raney nickel catalyst.

This process suffers from the distinct disadvantage of utilizing unsaturated aldonolactone as the starting material. There are relatively few unsaturated aldonolactones, which therefore limits the choice of hydrophilic moiety. The hydrophobic moiety must be balanced with the appropriate hydrophilic moiety for optimal detergency.

Accordingly, it is an object of the invention to provide a new process for the enzymatic manufacture of alkyl aldonolactone esters as carbohydrate-based surfactants.

It is another object of the invention to provide a new class of alkyl aldonolactone esters as effective carbohydrate-based surfactants that are biodegradable, mild and environmentally acceptable.

It is a particular object of the invention to prepare alkyl aldonolactone esters regioselectively in good color and high purity.

SUMMARY OF THE INVENTION

This invention relates to a new class of environmentally friendly, biodegradable "green" (i.e., made from naturally occurring, renewable raw materials) surfactants and a new process for their manufacture. The present invention also deals with an improvement over the art known process for the preparation of alkyl aldonolactone esters. The improvement comprises reacting an aldonolactone with an alkyl ester of fatty acid regioselectively in the presence of an enzyme (e.g., porcine pancreatic lipase, (PPL)). This invention is particularly directed to preparing alkyl aldonolactones in good color and high purity. Furthermore, the alkyl aldonolactone esters of the invention have surfactant properties comparable to petrochemically-derived surfactants.

DESCRIPTION OF SPECIFIC EMBODIMENTS

The present invention relates to a new class of environmentally friendly "green" surfactants that have both nonionic and anionic character as well as a new process for the manufacture of long-chained alkyl aldonolactone esters of the general formulas:

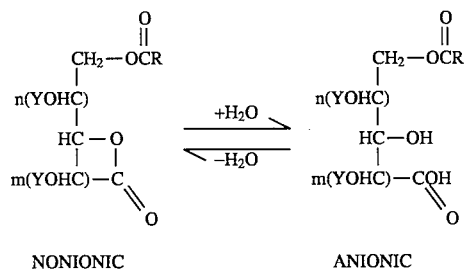

NONIONIC          ANIONIC wherein:

n=0–3 m=2–3

Y is a hydrogen atom, mono-, di- or oligosaccharide

R is a straight saturated alkyl radical containing 10 to 14 carbon atoms or branched alkyl or alkenyl radical which contains sufficient carbon atoms to be surface active but at least 6 carbons. The radical may also contain cycloaliphatic or polyalkyloxyalkyl groups comprising eight or more carbons.

Aldonolactones are obtained from the corresponding aldose by known chemical or enzymatic oxidation methods such as those disclosed in EP 0,142,725 (Kao Corp), EP 0,233,816 A1 (Roquette Freres), JP 0,111,648 (Kao Corp) and EP 232-202 A2 (Roquette Freres).

Suitable aldonolactones that may be used to form alkyl aldonolactone esters of the invention include, but are not limited to glucooctonolactone, glycero-manno-heptonolactone, gluconolactone, galactonolactone, mannolactone, ribonolactone, gulonolactone, lactobionolactone, maltobionolactone, erythronolactone and xylonolactone.

Suitable aliphatic hydrocarbon radicals may be saturated and unsaturated radicals including, but not limited to nonyl, decyl, undecyl, dodecyl, tridecyl, tetradecyl, pentadecyl, coco, soya and tallow; decenyl, dodecenyl, tetradecenyl, oleyl, noleyl and linolenyl. The active compounds of the invention may also contain straight or branched aliphatic groups. Cycloaliphatic radicals are exemplified, but not limited to cyclopentyl and cyclohexyl. Suitable alkyloxyalkyl radicals are exemplified by dodecyloxyethyl, dodecyloxyethyl, dodecyloxypropylene, dodecyloxypropyl, decyl-(dioxyethyl), tetradecyl(pentaoxyethyl), dodecyl(tetraoxypropyl), and tetradecyl(nonyloxypropylene).

In a preferred embodiment of the invention, suitable alkyl aldonolactone esters that may be used as carbohydrate surfactants in detergent, personal product, cosmetic and dental compositions are set forth below:

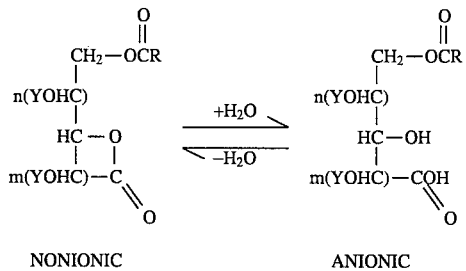

wherein:

n=0–3, m=2–3, Y is hydrogen and R is a substituted saturated or unsaturated or unsubstituted unsaturated radical having 8–18 carbons or an unsubstituted saturated radical having 10 to 14 carbons.

It has been found, in accordance with the present invention, that alkyl aldonolactone esters are carbohydrate-based surfactants that can exist in equilibrium in aqueous solution as a lactone, closed-ring nonionic form and an acid, opened-ring anionic form which is negatively charged.

The synthesis of alkyl aldonolactone esters, can be accomplished by regioselective esterification of an aldonolactone with a fatty acid ester in the presence of an enzymatic catalyst and organic solvent. Suitable fatty acid esters of the invention include, but are not limited to methyl alkanoates, ethyl alkanoates, propyl alkanoates, n-butyl alkanoates, isopropenyl alkanoates, oximine alkanoates, vinyl alkanoates, alkyl anhydrides, glycerides, or trihaloalkyl alkonates; however, trichloroethyl alkanoates are preferred.

Suitable enzymatic catalysts of the invention include, but are not limited to, lipases isolated from microorganisms such as bacteria, yeasts and molds, and are exemplified by those isolated from Humicula, Pseudomonas, Candida, Chromobacterium, Mucor, Rhizopus, Aspergillus and the like, lipases isolated from mammalian sources such as that isolated from porcine pancrease, esterases or other hydrolases including proteases. Porcine pancreatic lipase catalyst (PPL) is preferred. PPL was found to esterify the primary hydroxyl group of the aldonolactone selectively. Conversion of all aldonolactones to alkyl aldonolactone esters was determined by capillary gas chromatography after persilylation and found to range between 87 to 98% (Table 1).

TABLE 1

Enzymatic Reaction Time, Product Conversion and Yields

| Compound | Reaction Time (Hours) | % Conversion | % Isolated Yield |
| --- | --- | --- | --- |
| 6-O-Decyl-δ-Gluconolactone | 120 | 98.0 | 27.0 |
| 6-O-Decyl-δ-Gluconolactone | 72 | 91.0 | 26.0 |
| 6-O-Tetradecyl-δ-Gluconolactone | 120 | 97.0 | 46.0 |
| 5-O-Dodecyl-D-(+)-Ribonoδ-Lactone | 72 | 95.0 | 25.0 |
| 6-O-Dodecyl-D-Gulonoδ-Lactone | 72 | 87.0 | 32.5 |
| 7-)-Dodecyl α-D-Glucoheptonicδ-Lactone | 72 | 90.0 | 17.0 |

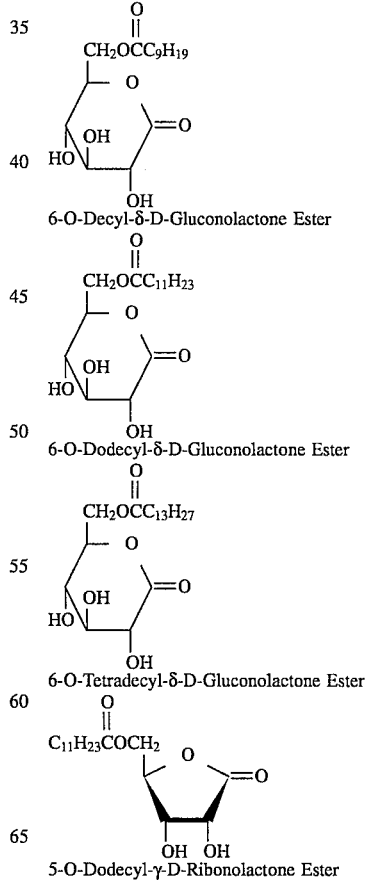

TABLE 1-continued

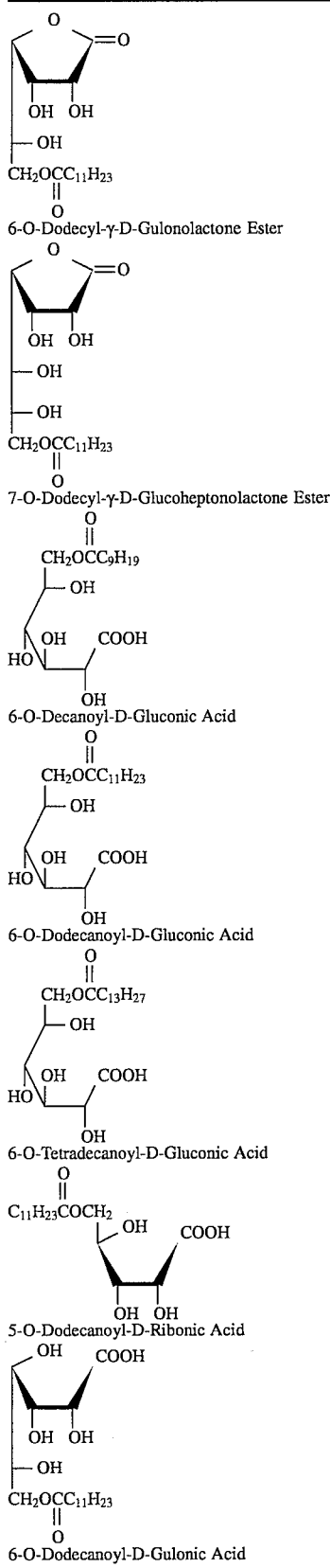

6-O-Dodecyl-γ-D-Gulonolactone Ester

7-O-Dodecyl-γ-D-Glucoheptonolactone Ester

6-O-Decanoyl-D-Gluconic Acid

6-O-Dodecanoyl-D-Gluconic Acid

6-O-Tetradecanoyl-D-Gluconic Acid

5-O-Dodecanoyl-D-Ribonic Acid

6-O-Dodecanoyl-D-Gulonic Acid

TABLE 1-continued

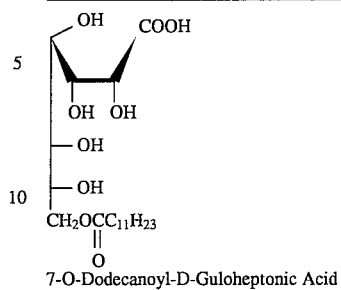

7-O-Dodecanoyl-D-Guloheptonic Acid

In accordance with Examples 1–7, the alkyl ester may be used in excess with respect to the aldonolactone used, however, stoichiometric molar amounts may also be employed. It is desirable to use water-free reaction components, however, small amounts of water are not objectionable. In the process of the invention, the alkyl ester may be added progressively, but is usually added in full amount at the beginning of the reaction with a molar ratio of 1 to 5 with respect to aldonolactone used.

The aldonolactone used in the method of the invention is preferably in fine powder form. The reaction is usually performed at elevated temperatures between about 30°–100° C., preferably at about 30°–50° C. but may also be performed at ambient temperature.

Solvents such as dimethylformamide, t-butanol, or pyridine may be used, however pyridine is usually preferred. The reactants are mixed with intensive stirring, since moderate stirring usually results in long reaction time (> 5 days) and slow reaction rates. The reaction time may vary depending on the aldonolactone selected, however 6–72 hours are preferred, and usually obtained (Table 2).

TABLE 2

Regioselective Acylation of the Primary Alcohol Group of Aldonolactones with 2,2,2 Trichloroethyl Dodecanoate Catalyzed by PPL

| Reaction Time (Hours) | % Conversion | | | |
| --- | --- | --- | --- | --- |
| | Ribono-γ-lactone | Glucoheptonic-γ-lactone | Glucono-lactone | Gulono-γ-lactone |
| 0 | 0 | 0 | 0 | 0 |
| 24 | 87 | 69 | 72 | 53 |
| 48 | 94 | 84 | 77 | 75 |
| 72 | 95 | 90 | 91 | 87 |

After the reaction is complete, the enzyme is removed by filtration and washed with an organic solvent. The organic solvent is then removed from the filtrate under reduced pressure and the resulting residue slurried with an organic solvent. Suitable organic solvents of the invention that may be used to slurry the crude product include, but are not limited to chloroform, petroleum ether, and acetonitrile. Insoluble solids are removed from the slurry by filtration followed by washing with an organic solvent. The purified filtrate is then made solvent-free by vacuum distillation and the resulting white, solid alkyl aldonolactone ester air dried.

Optionally, high purity alkyl aldonolactone esters may be obtained by recrystallization from 48–95% aqueous ethanol.

Because of their high degree of purity and good color, alkyl aldonolactone esters are well suited as biodegradable, mild surfactants for detergent, personal product, cosmetic, pharmaceutical and dental applications.

Examples and parts and proportions are present by weight unless otherwise noted.

EXAMPLE 1

Procedure for the Preparation of Alkyl Trichlorethyl Esters

Alkyl acid chloride (1 mol) was dispensed dropwise from a graduated funnel into a 500 mL round bottom flask containing a stirring solution of 2,2,2 trichloroethanol (1 mol). After one day, the product, 2,2,2 trichloroethanol alkylate is formed in >99% yield. Recovery of the product was achieved by dissolving in chloroform (two parts by volume) and transferring to a separatory funnel. The chloroform solution was washed with a dilute sodium bicarbonate solution (one part by volume) to remove any remaining HCl from the acylation reaction. The chloroform layer was then separated from the aqueous layer and dried with anhydrous sodium sulfate overnight. The sodium sulfate was then removed from the chloroform layer by filtration and the chloroform was removed by evaporation to obtain the product as a clear liquid.

EXAMPLE 2

Preparation of 6-O-Decyl-δ-Gluconolactone Ester

To pyridine (200 mL) containing δ-gluconolactone (47.60 mmol), 2,2,2 trichloroethyl decanoate (164.66 mmol) was added. The solution was stirred and equilibrated to 40° C. The crude porcine pancreatic lipase (48 g) was then added to the solution. The resulting non-homogenous solution was stirred for five days. After the fifth day, stirring of the mixture was stopped and the enzyme removed by filtration through a medium pore glass filter. The filtrate was then transferred to a 500 mL single neck round bottom flask and the solvent removed by evaporation. Following evaporation, a yellow mass was left in the flask. This yellow mass was then washed with chloroform (~100 mL) and filtered through a medium pore glass filter. The filtrate was then transferred to 500 mL single neck round bottom flask and the chloroform removed by evaporation. The residual material left in the flask was recrystallized from 95% ethanol to recover 4.3000 grams (99.20% pure) of 6-O-decyl-δ-gluconolactone ester as a white powder. mp 127.72° C.; $^{13}$C NMR (DMSO-d6) C6, C5, C4, C3, C2, C1 (δ 62.82, 74.00, 71.76, 68.33, 77.56, 172.61). For the decanoyl moiety $^{13}$C NMR (δ 13.85, 22.02, 24.36, 28.36, 28.58, 28.63, 28.77, 31.20, 33.31, 171.12); DRIFTS (KBr powder) 3473.64 cm$^{-1}$, 3390.84, 2956.34, 2922.15, 2853.08, 1749.20, 1715.48, 1469.05, 1167.28, 1061.96, 1011.7, 723.06; MS (NH$_4$) 330.20.

EXAMPLE 3

Preparation of 6-O-Dodecyl-δ-Gluconolactone Ester

To pyridine (50 mL) containing δ-gluconolactone (12.52 mmol), 2,2,2 trichloroethyl dodecanoate (36.22 mmol) was added. The solution was stirred and equilibrated to 40° C. The crude porcine pancreatic lipase (12 g) was then added to the solution. The resulting non-homogenous solution was stirred for three days. After the third day, stirring was stopped and the enzyme removed by filtration through a medium pore glass filter. The filtrate was then transferred to a 50 mL single neck round bottom flask and the solvent removed by evaporation. Following evaporation a yellow mass was left in the flask. This yellow mass was washed with chloroform (~25 mL) and filtrated through a medium pore glass filter. The filtrate was then transferred to 50 mL single neck round bottom flask and the chloroform removed by evaporation. The residual material was recrystallized from 95% ethanol to recover 1.2236 grams (97.00% pure) of 6-O-dodecyl-δ-gluconolactone ester as a white powder. mp: 120.89° C.; $^{13}$C NMR (DMSO-d6) C6, C5, C4, C3, C2, C1 (δ 62.80, 74.02, 71.74, 68.35, 77.56, 172.54). For the dodecanoyl moiety $^{13}$C NMR (δ 13.78, 21.97, 24.32, 28.32, 28.58, 28.58, 28.76, 28.76, 28.88, 31.19, 33.28, 171.03); DRIFTS (KBr powder) 3476.09 cm$^{-1}$, 3389.31, 2956.22, 2920.74, 2852.00, 1748.92, 1716.06, 1469.70, 1166.85, 1061.92, 1007.96, 722.31; MS (NH$_4$) 360.10.

EXAMPLE 4

Preparation of 6-O-Tetradecyl-δ-Gluconolactone Ester

To pyridine (200 mL) containing δ-gluconolactone (47.60 mmol), 2,2,2 trichloroethyl tetradecanoate (138.98 mmol) was added. The solution was stirred and equilibrated to 40° C. Then crude porcine pancreatic lipase (48 g) was added to the solution. The resulting non-homogenous solution was stirred for 5 days. After the fifth day, stirring was stopped and the enzyme removed by filtration through a medium pore glass filter. The filtrate was then transferred to a 500 mL single neck round bottom flask and the solvent removed by evaporation. Following evaporation, a yellow mass was left in the flask. This yellow mass was then washed with ice cold petroleum ether (~100 mL) and filtered through a medium pore glass filter. The filtrate was then transferred to 500 mL single neck round bottom flask and the petroleum ether removed by evaporation. The residual material left in the flask was recrystallized from 95% ethanol to recover a total of 8.5312 grams (93.00% pure) of 6-O-tetradecyl-δ-gluconolactone ester as a white powder. mp 144.29° C.: $^{13}$C NMR (DMSO-d6) C6, C5, C4, C3, C2, C1 (δ 62.87, 74.03, 71.79, 68.36, 77.60, 172.61). For the tetradecanoyl moiety $^{13}$C NMR (δ 13.86, 22.06, 24.39, 26.68, 26,68, 28.41, 28.87, 28.87, 28.99, 28.99, 28.99, 31.28, 33.33, 171.14); DRIFTS (KBr powder) 3477.87 cm$^{-1}$, 3385.28, 2956.24, 2919.56, 2851.47, 1748.3, 1715.84, 1470.77, 1174, 1165.74, 1061.30, 1011.77, 721.04; MS (NH$_4$) 388.20.

EXAMPLE 5

Preparation of 6-O-Dodecyl D-Gulonic-γ-Lactone Ester

To pyridine (50 mL) containing D-gulonic-γ-lactone (12.21 mmol), 2,2,2 trichloroethyl dodecanoate (36.22 mmol) was added. The solution was stirred and equilibrated to 40° C. Then crude porcine pancreatic lipase (12 g) was added to the stirring solution. The resulting non-homogenous solution was stirred for three days. After the third day, the stirring of the mixture was stopped and the enzyme removed by filtration through a medium pore glass filter. The filtrate was then transferred to a 50 mL single neck round bottom flask and the solvent removed by evaporation. Following evaporation, a yellow mass was left in the flask. This yellow mass was then washed with chloroform (~25 mL) and filtered through a medium pore glass filter. The filtrate was then transferred to 50 mL single neck round bottom flask and the chloroform removed by evaporation. The, residual material left in the flask was recrystallized from 48% ethanol to recover 1.4368 grams (96.00% pure) of 6-O-decyl-D-gulonic-γ-lactone ester as a white powder. mp 106.39° C.; $^{13}$C NMR (DMSO-d6) C6, C5, C4, C3, C2, C1 (δ 64.40, 69.18, 80.28, 67.24, 70.64, 175.75). For the dodecanoyl moiety $^{13}$C NMR (δ 13.80, 22.03, 24.36, 28.47, 28.53, 28.53, 28.67, 28.67, 28.88, 31.26, 33.40, 172.77); DRIFTS (KBr powder) 3492.79 cm$^{-1}$, 3452.4, 3343.18, 2958.11, 2917.15, 2849.50, 1779.79, 1722.35, 1464.93, 1181.28, 1147.05, 771.61, 723.07; MS (NH$_4$) 360.2.

EXAMPLE 6

Preparation of 5-O-Dodecyl D-(+)-Ribonic-γ-Lactone Ester

To pyridine (50 mL) containing D-(+)-ribonic-δ-lactone (12.50 mmol), 2,2,2 trichloroethyl dodecanoate (37.45 mmol) was added. The solution was stirred and equilibrated to 40° C. Then crude porcine pancreatic lipase (12 g) was added to the stirring solution. The resulting non-homogenous solution was stirred for three days. After the third day, the stirring of the mixture was stopped and the enzyme removed by filtration through a medium pore glass filter. The filtrate was then transferred to a 50 mL single neck round bottom flask and the solvent removed by evaporation. Following evaporation, a yellow mass was left in the flask. This yellow mass was then washed with acetonitrile (~30 mL) and filtered through a medium pore glass filter. The precipitate was recovered and recrystallized from 48% ethanol to obtain 1.0286 grams (99.99% pure) of 5-O-dodecyl D-(+)-ribonic-γ-lactone ester as a white powder, mp 134.74° C.: $^{13}$C NMR (DMSO-d6) C5, C4, C3, C2, C1 (δ 62.77, 81.84, 68.70, 68.19, 175.48). For the dodecanoyl moiety $^{13}$C NMR (δ 13.80, 21.96, 24.25, 28.28, 28.55, 28.55, 28.75, 28.75, 28.87, 31.18, 33.21, 172.35); DRIFTS (KBr powder) 3484.81 cm$^{-1}$, 3292.84, 2981.50, 2852.62, 1753.49, 1469.41, 1192.25, 1159.52, 778.085, 718.04; ATR (Chloroform:Methanol{1:1}) 2928.78 cm$^{-1}$, 1785.26, 1742.72, 1148.29, 1024.48, 759.06; MS (NH$_4$) 330.2.

EXAMPLE 7

Preparation of 7-O-Dodecyl α-D-Glucoheptonic-γ-Lactone Ester

To pyridine (50 mL) containing α-D-glucoheptonic-γ-lactone (12.50 mmol), 2,2,2 trichloroethyl dodecanoate (36.19 mmol) was added. The solution was stirred and equilibrated to 40° C. Then crude porcine pancreatic lipase (12 g) was added to the stirring solution. The resulting non-homogenous solution was stirred for three days. After the third day, the stirring of the mixture was stopped and the enzyme removed by filtration through a medium pore glass filter. The filtrate was then transferred to a 50 mL single neck round bottom flask and the solvent removed by evaporation. Following evaporation, a yellow mass was left in the flask. This yellow mass was then washed with chloroform (~30 mL) and filtered through a medium pore glass filter. The filtrate was then transferred to 50 mL single neck round bottom flask and the chloroform removed by evaporation. The residual material left in the flask was recrystallized from 95% ethanol to recover 0.8500 grams (99.00% pure) of 7-O-dodecyl α-D-glucoheptonic-γ-lactone ester as a white powder. mp 112.33° C.; $^{13}$C NMR (DMSO-d6) C7, C6, C5, C4, C3, C2, C1 (δ 65.06, 68.23, 70.47, 79.13, 70.84, 70.34, 175.82). For the dodecanoyl moiety $^{13}$C NMR C1 (δ 13.80, 22.00, 24.36, 28.44, 28.63, 28.63, 28.67, 28.67, 28.84, 31.23, 33.46, 172.86); DRIFTS (KBr powder) 3427.37 cm$^{-1}$, 2954.44, 2920.06, 2852.66, 1775.92, 1745.35, 1707.33, 1471.75, 1418.96, 1175.76, 1098.02, 720.31; MS (NH$_4$) 390.3.

EXAMPLES 8–11

Surfactancy

In order to demonstrate the effectiveness of these compounds as surfactants, various physical properties such as Krafft Point, foam height and foam dissolution were measured. The results are set forth in Examples 8–10.

EXAMPLE 8

Krafft Point

The temperature at which a surfactant begins to form micelles instead of precipitates is referred to as the Krafft Point. The appearance and development of micelles are important, since detergency and the solubilization of soils depend on the formation of these aggregates in solution. In general, surfactants with low Krafft Point values are preferred, but not always necessary because compositions which contain highly soluble surfactants often dissolve less soluble surfactants, resulting in the optimum balance for detergency.

The Krafft Points of various alkyl aldonolactone esters are set forth below:

| Compound | Cp | Kf Aldono-lactone Ester/ Aldonic Acid Mixture | Cp Aldono-lactone Ester/ Aldonic Acid Mixture |
| --- | --- | --- | --- |
| 6-O-Decyl-δ-Glucono-lactone | 90° C. | 30° C. | 60° C. |
| 6-O-Dodecyl-δ-Gluconolactone | 96° C. | 37° C. | 65° C. |
| 6-O-Tetradecyl-δ-Gluconolactone | 90° C. | 50° C. | — |
| 5-O-Dodecyl D-(+)-Ribono-γ-Lactone | >100° C. | — | — |
| 6-O-Dodecyl D-Gulono-γ-Lactone | 90° C. | 30° C. | 70° C. |
| 7-O-Dodecyl α-D-Glucoheptonic-γ-Lactone | 90° C. | 55° C. | 56° C. |

The Krafft Point was measured by preparing a 0.1% by weight dispersion of alkyl aldonolactone ester in water. From room temperature, the dispersion was slowly heated (0.5°–1.0° C.) until the solution became clear. At that temperature, the clearpoint (Cp) was recorded. The solution was then slowly cooled until precipitation occurs. At that temperature, the Krafft Point point was recorded and found to correspond to an equilibrium mixture (~2:1) of alkyl aldonic acid and alkyl aldonolactone. This was confirmed by GC/MS and NMR studies. The aqueous solution was again heated until clear and a second Cp was recorded which corresponded to the clear point of the alkyl aldonolactone and alkyl aldonic acid mixture.

EXAMPLE 9

Foam Stability

The generation of a thick stable foam is important because consumers are accustomed to, and expect, compositions to produce a copious and rich foam. Compositions that do not generate sufficient foam are often seen as inferior. Accordingly, we have found that the aldonolactone esters of the invention unexpectedly stabilize and enhance the foam of SDS, a commonly used anionic surfactant very effectively.

In order to demonstrate the improved ability of aldonolactone esters to stabilize and enhance foam, 0.1% solutions of 100:0, 75:25, 50:50, and 0:100 6-O-dodecyl-γ-gluconolactone/SDS were tested according to the Ross-Miles foam height assay (ASTM D1173-53; Oil and Soap (1958), 62:1260).

In the Ross-Miles method, 200 mL of a solution of surfactant contained in a pipette of specified dimensions with a 2.9-mm-i.d. orifice is allowed to fall 90 cm onto 50 mL of the same solution contained in a cylindrical vessel maintained at a given temperature by means of a water jacket. The height of the foam produced in the cylindrical vessel is read immediately after all the solution has run out of the pipette and then again after a given amount of time.

Using this method, the foam production (initial foam height) and foam stability (final foam height after 15 minutes) were measured at 60° C. and 0 ppm (parts per million) water hardness.

The results are set forth below:

TABLE 1

Ross-Miles Foam Height Assay
6-O-Dodecyl-δ-Gluconolactone/Sodium Dodecyl Sulfate
Mixed Systems (0.1%), 60° C.

|  | FOAM HEIGHT (mm) | |
| --- | --- | --- |
|  | INITIAL | FINAL |
| 100% SDS<br>0% 6-O-dodecyl-δ-gluconolactone | 90 | 4 |
| 75% SDS<br>25% 6-O-dodecyl-δ-gluconolactone | 195 | 123 |
| 50% SDS<br>50% 6-O-dodecyl-δ-gluconolactone | 211 | 126 |
| 0% SDS<br>100% 6-O-dodecyl-δ-gluconolactone | 171 | 144 |

As indicated by the above table, 6-O-dodecyl-γ-gluconolactone was found to enhance and stabilize the foam of sodium dodecyl sulfate (SDS). This enhancement was largest when the ratio of SDS to 6-O-dodecyl-δ-gluconolactone was 50:50.

EXAMPLE 10

Detergency Evaluation

The detergency performance of 6-O-dodecyl-γ-gluconolactone was evaluated on a Lever clay cloth (65/35 polyester/cotton cloth coated with ditallow, dimethylamine, cation/ kaolinitic clay/quartz mixture) using a tergotometer. The performance of 6-O-dodecyl-γ-gluconolactone was compared to a typical detergent anionic surfactant, linear alkylbenzenesulfonate, alone and as a mixed active system (75:25, 50:50 and 14:86 anionic:nonionic surfactant ratio). A non-phosphate, zeolite-built burkite base powder was dosed over the side at about 1.0 g/L. The system was kept at 40° C., pH= 10 for 30 minutes.

Improvement on detergency was measured by a change in reflectance (ΔR) of the stained cloth, before and after washing with the surfactant prototype. In general, larger reflectance values suggest better detergency.

The detergency performance of 6-O-dodecyl-γ-gluconolactone is set forth below:

| Active Ratio<br>Linear Alkylbenzenesulfonate:<br>6-O-Dodecyl-γ-Gluconolactone | ΔR |
| --- | --- |
| 100:0 | 14.4 |
| 75:25 | 19.4 |
| 50:50 | 18.1 |
| 14:86 | 17.3 |
| 0:100 | 5.0 |

As can be seen from the above table, the addition of 6-O-dodecyl-γ-gluconolactone to linear alkylbenzenesulfonate at 25–86% shows better or enhanced detergency when compared to linear alkylbenzenesulfonate alone. The ΔR was measured using a Gardiner Reflectometer and the formulations and test cloths are as follows:

| Ratio of Surfactants<br>Cloth:Lever Clay<br>Ester<br>LAS:Aldonolactone Ester | Actual Formulation<br>BP:LAS:Aldonlactone | | |
| --- | --- | --- | --- |
| 100:0 | 77.3:22.7:0 | | |
| 75:25 | 77.3:17:5.7 | | |
| 50:50 | 77.3:11.35:11.35 | | |
| 14:86 | 77.3:3.18:19.52 | | |
| 0:100 | 77.3:0:22.7 | | |
| BP | = | .75 g/l = | 77.3% |
| Total Surfactant | = | .22 g/l = | 22.7% |
|  |  | .97 g/l | 100.0% |

LAS = Linear Alkylbenzenesulfonate
Ester = 6-O-Dodecyl-δ-Gluconolactone
BP = Burkeite Base Powder = 0.45 g/l zeolite 4A + 0.30 g/l $Na_2CO_3$ = 0.75 g/l

EXAMPLE 11

Zein Solubilization Assay

The zein solubilization assay was developed to determine the biological effects of surfactants on the skin. This protein is normally insoluble in water but can be brought into solution by interaction with surfactants. The extent of zein dissolved is related to the irritation potential of a surfactant. Thus, the greater the zein solubilization, the greater the irritation potential (M. J. Schwinges, Kolloid-Z.Z. PO. (1969), 233, 848).

In order to demonstrate the ability of aldonolactone esters to provide mildness benefits to the skin, a mixture of 6-O-dodecyl-γ-gluconolactone and SDS were tested and compared to pure SDS. Thus, a 1% solution of surfactant (30 mL) was added to 1.5 g zein and stirred at 40° C. for one hour. Residual zein was collected and dried to constant weight. Differences between starting and residual weights were used to calculate percentage of zein solubilized. The results are set forth below:

| Active Ratio<br>(6-O-Dodecyl-γ-<br>Gluconolactone:SDS) | % Zein Solublized |
| --- | --- |
| 0:100 | 78.3 |
| 50:50 | 21.7 |

As indicated by the above table, the addition of 6-O-dodecyl-γ-gluconolactone to SDS (50:50) results in less zein solubilization. This finding suggests that the formulation is more mild than SDS alone and so aldonolactone esters not only enhance and stabilize foam, but they reduce the irritation potential of SDS on the skin.

EXAMPLE 12

Compositions

In one embodiment of the invention, an alkyl aldonolactone ester is used as a surfactant in a detergent composition. An example of a specific alkyl aldonolactone ester is set forth below:

Wherein, in each case, R is a substituted or unsubstituted saturated or unsaturated alkyl group having 6–24 carbons, preferably 8–18 carbons R may also be an alkoxylated alkyl chain and the alkyl aldonolactone ester may be ethoxylated and propoxylated or mixtures thereof.

Because of their favorable surfactant properties, alkyl aldonolactone esters are well suited for detergent, personal product, cosmetic, pharmaceutical and dental applications, particularly powdered, light or heavy-duty liquid detergent compositions.

Examples of powdered detergent compositions are described in U.S. Pat. No. 4,929,379 to Oldenburg et al. and of light-duty liquid detergent compositions are described in U.S. Pat. No. 4,671,894 to Lamb et al., U.S. Pat. No. 4,368,146 to Aronson et al. and U.S. Pat. No. 4,555,360 to Bissett et al., all of which are hereby incorporated by reference into the subject application.

Examples of a heavy-duty liquid detergent composition are described in U.S. Pat. No. 4,959,179 to Aronson et al. which is hereby incorporated by reference into the subject application.

A powdered detergent composition might contain the following (all percentages are by weight)

| (1) 1–40% | Alkyl Aldonolactone Ester |
| (2) 5–40% | Additional Surface Active Agent |
| (3) 0–50% | Builder or Sequestering Agent |
| (4) 0–40% | Buffering Agent |
| (5) 0–30% | Electrolyte |
| (6) 0–20% | Bleach System |
| (7) 0.1–5% | Enzyme |
| (8) Balance | Minors Plus Water to 100% |

Powdered detergent compositions of the invention can comprise from about 1–60% alkyl aldonolactone ester, preferably 1–40%; from about 5–70% additional surface active agent, preferably 5–40%; from about 0–70% builder, preferably 15–50%; from about 0–60%; buffering agent preferably 0–40%; from 0–50% electrolyte; from 0–10% enzyme, preferably 0.1–5% and the balance being minor ingredients and water.

A liquid detergent composition might contain the following (all percentages are by weight)

| (1) 1–50% | Alkyl Aldonolactone Ester |
| (2) 5–70% | Additional Surface Active Agent |
| (3) 0–20% | Builder or Sequestering Agent |
| (4) 0.15% | Electrolyte |
| (5) 0.1–5% | Enzyme |
| (6) 0.1–15% | Enzyme Stabilizer |
| (7) 0–20% | Phase Regulant |
| (8) Balance | Minors Plus Water to 100% |

Liquid detergent composition of the invention can be built or unbuilt and may be aqueous or nonaqueous. The compositions generally comprise from 1–70% alkyl aldonolactone ester, preferably 1–50%; from 5–80% additional surface active agent, preferably 5–70%; from 0–50% builder, preferably 0–20%; from 0–60% electrolyte, preferably 0–15%; from 0–10% enzyme, preferably 0.1–5%; from 0.1–30% enzyme stabilizer, preferably 0.1–15%; from 0–30% phase regulant preferably 0–20% and the balance minors and water.

Suitable detergent surface active agents of the invention that can be used are C10 to C24 carbon atom fatty acid soaps, anionic, nonionic, cationic, zwitterionic or amphoteric synthetic surfactants, or mixtures thereof, however, anionic and nonionic synthetic surfactants are preferred.

Examples of anionic synthetic surfactants that can be used are salts (including sodium, potassium, ammonium and substituted mono, di- and triethanolamine salts) of 8 to 20 carbon alkylbenzenesulfonates, 8 to 20 carbon primary or secondary alkanesulfonates 8 to 20 carbon olefin sulfonates, 8 to 20 carbon alkylsulfate, 8 to 20 carbon alkylpolyglycolether sulfate and carboxylates containing up to 12 ethylene oxide units. Any suitable anionic surfactant may be used, however, 8 to 20 carbon alkylbenzenesulfonates and primary alkanesulphonates are preferred.

Examples of nonionc synthetic surfactants that can be used are condensation products of ethylene oxide and propylene oxide with 8 to 20 carbon alcohols, 8 to 20 carbon, alkylphenols or 8 to 20 carbon fatty acid amides. Any suitable nonionic surfactant may be used, however, 8 to 20 carbon ethoxylated alcohol containing 3 to 12 ethylene oxide units are preferred.

Builders that can be used according to this invention include conventional alkaline detergency builders, inorganic or organic as well as zeolites and the like.

Examples of suitable inorganic alkaline detergency builders are water-soluble alkalimetal phosphates, polyphosphate, borates, silicates and carbonates.

Examples of suitable organic alkaline detergency builders are polycarboxylate builders such as water soluble salts of citric acid, mettitic acid, carboxymethyloxy succinic acid and salts of polymers of itaconic acid and maleic acid. Other polycarboxylate builders include DPA (dipicolinic acid, and ODS (oxydisuccinic acid). Zeolites and aluminosilicates of the formula $Na_x[(AlO_2)y \cdot (SiO_2)]zH_2O$ wherein x and y are integers of 6 and z is an integer from about 15 to 264 are preferred. Any suitable builders may be used, however, zeolites are preferred.

The alkaline buffering agent can be any such agent capable of providing a 1% product solution with a pH above 9. Advantageous alkaline buffering agents are the alkalimetal silicates, since they decrease the corrosion of metal parts in washing machines and in which various sodium silicates are preferred.

The liquid detergent compositions may comprise an amount of electrolyte (defined as a water-soluble salt) whose quantity depends on whether or not the composition is structured. By structured is meant the formation of, lamellar phase sufficient to endow solid suspending capability.

The water-soluble electrolyte salt may be a detergency builder, such as sodium tripolyphosphate or it may be a non-functional electrolyte such as sodium sulfate or sodium chloride. Preferably, whatever builder is used in the composition comprises all or part of the electrolyte.

Enzymes which can be used are proteases, lipases, amylases and cellulases or mixtures thereof.

Stabilizers or stabilizer systems may be used in conjunction with enzymes and may comprise calcium chloride, calcium acetate, propionic acid salt, boric acid, boric oxide, borax, alkali metal borates (e.g., sodium ortho-, meta- and pyroborate) or polyols such as propylene glycol, ethylene glycol, glycerol, sorbitol, mannitol and glucose. The especially preferred stabilization system is boric acid in combination with a polyol. Preferably, the weight ratio of polyol to boric acid added is at least 1:1, more preferably about 1.3 to 1.

In addition to the ingredients described hereinbefore, the preferred compositions herein frequently contain a series of optional ingredients which are used for the known functionality in conventional levels. While the detergent compositions are generally premised on aqueous, enzyme-containing detergent compositions, it is frequently desirable to use a phase regulant. This component together with water constitutes then the solvent matrix for the claimed liquid compositions. Suitable phase regulants are well-known in liquid detergent technology and, for example, can be represented by hydrotropes such as salts of alkylarylsulfonates having up to 3 carbon atoms in the alkylgroup, e.g., sodium, potassium, ammonium and ethanolamine salts of xylene-, toluene-, ethylbenzene-, cumene-, and isopropylbenzene sulfonic acids. Alcohols may also be used as phase regulants. This phase regulant is frequently used in an amount from about 0.5% to about 20%, the sum of phase regulant and water is normally in the range from 35% to 65%.

Examples of oxygen or chlorine liberating bleaches that may be used are dichlorocyanuric acid salts one alkalimetal hypochlorides.

The preferred compositions herein can contain a series of optional ingredients which are mostly used in minor additive levels, usually below about 5%. Examples of these additives include: suds regulants; lather depressants; opacifiers; antioxidants; bactericides; germicides; optical brighteners; antitarnishing agents; dyes; fabric softening agents and perfumes.

The personal product compositions of the invention may be, for example, toilet bar compositions, facial or body cleansing compositions, shampoos for hair or body, conditioners, cosmetic compositions, dental compositions, or light duty liquids.

In a second embodiment of the invention, the alkyl aldonolactone ester surfactant of the invention may be used, for example, in a toilet bar (i.e., soap and/or detergent bar) formulation.

Typical toilet bar compositions are those comprising fatty acid soaps used in combination with a detergent other than fatty acid soap and free fatty acids. It should be noted that the composition may comprise fatty acid soap and may be based merely on actives other than fatty acid soap. Mildness improving salts, such as alkali metal salt or isethionate, are also typically added. In addition other ingredients, such as germicides, perfumes, colorants, pigments, suds-boosting salts and anti-mushing agents may also be added.

Fatty acid soaps are typically alkali metal or alkanol ammonium salts of aliphatic alkane or alkene monocarboxylic acids. Sodium, potassium, mono-, di- and triethanolammonium cations, or combinations thereof, are suitable for purposes of the invention.

The soaps are well known alkali metal salts of natural or synthetic aliphatic (alkanoic or alkenoic) acids having about 8 to 22 carbons, preferably 12 to about 18 carbons.

Examples of soap which may be used may be found in U.S. Pat. No. 4,695,395 to Caswell et al. and U.S. Pat. No. 4,260,507 (Barrett), both of which are incorporated herein by reference.

In a soap-based bar, fatty acid soaps will generally comprise greater than 25% of the composition, generally from 30–95%. Preferably, the amount of soap will range from 40% to 70% by weight of the composition. In a bar based on other actives, soap may comprise 0–50% by weight.

The compositions will also generally comprise a non-soap detergent which is generally chosen from anionic, nonionic, cationic, zwitterionic or amphoteric synthetic detergent materials or mixtures thereof. These surfactants are all well known in the art and are described, for example, in U.S. Pat. Nos. 4,695,395 and 4,260,507 discussed above. One preferred non-soap anionic is a $C_8$–$C_{22}$ akyl isethionate. This ester may be prepared by the reaction between alkali metal isethionate and mixed aliphatic fatty acids having from 8 to 22 carbons. The non-soap actives may comprise from 0 to 50% of the composition.

A certain amount of free fatty acids of 8 to 22 carbons are also desirably incorporated into soap compositions to act as superfatting agents or as skin feel and creaminess enhancers. If present, the free fatty acids comprise between 1 and 40% of the compositions.

A preferred salt which may be added to soap compositions is a simple unsubstituted sodium isethionate. This may be present as 0.1 to 50% of the composition, preferably 0.5% to 25%, more preferably 2% to about 15% by weight. Other mildness co-actives which may be used include betain compounds or ether sulphates. These also may be present at 0.1 to 50% of the composition, preferably 0.5% to 25%.

Other optional ingredients which may be present in toilet bar compositions are moisturizers such as glycerin, propylene glycol, sorbitol, polyethylene glycol, ethoxylated or methoxylated ether of methyl glucose etc; water-soluble polymers such as collagens, modified celluloses (such as POLYMER JR®), guar gums and polyacrylates; sequestering agents such as citrate, and emollients such as silicones or mineral oil.

In a third embodiment of the invention, the alkyl aldonolactone ester surfactant of the invention may be present in a facial or body cleansing composition. Examples of such cleaning compositions are described, for example, in U.S. Pat. No. 4,812,253 to Small et al. and U.S. Pat. No. 4,526,710 to Fujisawa, both of which are hereby incorporated by reference.

Typically, cleansing compositions will comprise a fatty acid soap together with a non-soap surfactant, preferably a mild synthetic surfactant. Cleaning compositions will also generally include a moisturizer or emollient and polymeric skin feel and mildness aids. The compositions may further optionally include thickener (e.g., magnesium aluminum silicate, CARBOPOL®), conditioners, water soluble polymers (e.g., carboxymethyl cellulose), dyes, hydrotropes, brighteners, perfumes and germicides.

The fatty acid soaps used are such as those described above in uses in detergent bar formulations. These soaps are typically alkali metal or alkanol ammonium salts of aliphatic or alkene monocarboxylic salts. Sodium, potassium, mono-, di- and triethanol ammonium cations, or combinations thereof are suitable. Preferred soaps are 8 to 24 carbon half acid salts of, for example, triethanolamine.

Surfactants can be chosen from anionic, nonionic, cationic, zwitterionic or amphoteric materials or mixtures thereof such as are described in U.S. Pat. No. 4,695,395 mentioned above, or in U.S. Pat. No. 4,854,333 to Inman et al., hereby incorporated by reference.

Moisturizers are included to provide skin conditioning benefits and improve mildness. This term is often used as synonymous with emollient and is then used to describe a material which imparts a smooth and soft feeling to skin surface.

There are two ways of reducing water loss from the stratum corneum. One is to deposit on the surface of the skin an occlusive layer which reduces the rate of evaporation. The second method is to add nonocclusive hygroscopic substances to the stratum corneum which will retain water, and make this water available to the stratum corneum to alter its physical properties and produce a cosmetically desirable effect. Nonocclusive moisturizers also function by improving the lubricity of the skin.

Both occlusive and nonocclusive moisturizers can work in the present invention. Some examples of moisturizers are long chain fatty acids, liquid water-soluble polyols, glycerin, propylene glycol, sorbitol, polyethylene glycol, ethoxylated/propoxylated ethers of methyl glucose (eg., methyl gluceth-20) and ethoxylated/-propoxylated ethers of lanolin alcohol (e.g., SOLULAN®-75).

Preferred moisturizers are coco and tallow fatty acids. Some other preferred moisturizers are the nonoclusive liquid water soluble polyols and the essential amino acid compounds found naturally in the skin.

Other preferred nonocclusive moisturizers are compounds found to be naturally occurring in the stratum corneum of the skin, such as sodium pyrrolidone carboxylic acid, lactic acid, urea, L-proline, guanidine and pyrrolidone. Examples of other nonocclusive moisturizers include hexadecyl, myristyl, isodecyl or isopropyl esters of adipic, lactic, oleic, stearic, isostearic, myristic or linoleic acids, as well as many of their corresponding alcohol esters (sodium isostearoyl-2 lactylate, sodium capryl lactylate), hydrolyzed protein and other collagen-derived proteins, aloe vera gel and acetamide MEA.

Some occlusive moisturizers include petrolatum, mineral oil, beeswax, silicones, lanolin and oil-soluble lanolin derivatives, saturated and unsaturated fatty alcohols such as behenyl alcohol, squalene and squalane, and various animal and vegetable oils such as almond oil, peanut oil, wheat germ oil, linseed oil, jojoba oil, oil of apricot pits, walnuts, palm nuts, pistachio nuts, sesame seeds, rapeseed, cade oil, corn oil, peach pit oil, poppyseed oil, pine oil, castor oil, soybean oil, avocado oil, safflower oil, coconut oil, hazelnut oil, olive oil, grape seed oil and sunflower seed oil.

Other examples of both types of moisturizers are disclosed in "Emollients—a Critical Evaluation," by J. Mausner, Cosmetics & Toiletries, May, 1981, incorporated herein by reference.

The Polymeric skin feel and mildness aids useful in the present invention are the cationic, anionic, amphoteric, and the nonionic polymers used in the cosmetic field. Reduced skin irritation benefits as measured by patch testing of cationic and nionionic types of polymers are set out in "POLYMER JR® for Skin Care" Bulletin, by Union Carbide, 1977. The cationics are preferred over the others because they provide better skin feel benefits.

The amount of polymeric skin feel and mildness aids found useful in the composition of the present invention is from about 0.01% to about 5%, preferably from about 0.3% to about 4%. In bar compositions with less than 5.5% soap, the polymer is used at a level of 2% to 5%, preferably 3% or more.

Other types of high molecular weight polymeric skin feel and skin mildness aids, such as nonionic guar gums, MERQUATS® 100 and 550, made by Merck & Co, Inc.; JAGUAR® C-14-S made by Stein Hall; MIRAPOL® A15 made by Miranol Chemical Company, Inc.; and GALACTASOL® 811, made by Henkel, Inc.; plus others, are usable. The polymer also provides enhanced creamy lather benefits.

The nonionic polymers found to be useful include the nonionic polysaccharides, e.g., nonionic hydroxypropyl guar gums, offered by Celanese Corp. A preferred nonionic hydroxypropyl guar gum material is JAGUAR® HP-60 having molar substitution of about 0.6. Another class of useful nonionics is the cellulosic nonionic polymers, e.g., HEC and CMC.

The cationic polymers employed in this invention also provide a desirable silky, soft, smooth in-use feeling. The preferred level for this invention is 0.1–5% of the composition. There is reason to believe that the positively charged cationic polymers can bind with negatively charges sites on the skin to provide a soft skin feel after use. Not to be bound by any theory, it is believed that the greater the charge density of the cationic polymer, the more effective it is for skin feel benefits.

Other suitable cationic polymers are copolymers of dimethylaminoethylmethacrylate and acrylamide and copolymers of dimethyldiallylammonium chloride and acrylamide in which the ratio of the cationic to neutral monomer units has been selected to give a copolymer having a cationic charge. Yet other suitable types of cationic polymers are the cationic starches, e.g., STA-LOK® 300 and 400 made by Staley, Inc.

A more complete list of cationic polymers useful in the present invention is described in U.S. Pat. No. 4,438,095, to Grollier/allec, issued Mar. 20, 1984, incorporated herein by reference. Some of the more preferred cationics are listed in Col. 3, Section 2; Col. 5, section 8; Col. 8, section 10; and Col. 9, lines 10–15 of the Grollier/allec patent, incorporated herein by reference.

In a fourth embodiment of the invention, the alkyl aldonolactone ester surfactant of the invention may be used, for example, in a bar or body shampoo. Examples of such compositions are described in U.S. Pat. No. 4,854,333, to Inman and U.S. Pat. No. 4,526,710 to Fujisawa, both of which are hereby incorporated by reference.

The shampoo compositions which may be used typically comprise a surfactant selected from any one of a wide variety of surfactants known in the art (such as those described in U.S. Pat. No. 4,854,333, incorporated herein by reference). The shampoo compositions may additionally comprise a compound considered useful for treating dandruff, e.g. selenium sulfide.

The compositions all may also optionally comprise a suspending agent, for example, any of several acyl derivative materials or mixtures thereof. Among these are ethylene glycol esters of fatty acids having 16 to 22 carbons. Preferred suspending agents include ethylene glycol stearates, both mono- and distearate. Preferred alkanol amides are stearic monoethanolamide, stearic diethanolamide and stearic monoisopropanolamide. Still other long chain acyl derivatives include long chain esters of long chain fatty acids (e.g., stearyl stearate, cetyl palmitate), glyceryl esters (e.g. glyceryl distearate), and long chain esters of long chain alkanol amides (e.g., stearamide DEA distearate, stearamide MEA stearate).

Still other suitable suspending agents are alkyl (16 to 22 carbon) dimethyl amine oxides, such as stearyl dimethyl amine oxide. If the compositions contain an amine oxide or a long chain acyl derivative as a surfactant, these components may also provide the suspending function and additional suspending agent may not be needed.

Xanthan gum is another agent used to suspend, for example, selenium sulfide which may be in the present compositions. This biosynthetic gum material is commercially available and is a heteropolysaccharide with a molecular weight of greater than 1 million. It is believed to contain D-glucose, D-mannose and D-glucuronate in the molar ratio of 2.8:2.0:2.0. The polysaccharide is partially acetylated with 4.7% acetyl. Supplemental information on these agents is found in Whistler, Roy L. (Editor), *Industrial Gums—Polysaccharides and Their Derivatives* New York: Academic Press, 1973. Kelco, a Division of Merck & Co., Inc., offers xanthan gum as KeltrolR.

A Particularly preferred suspending system comprises a mixture of xanthan gum, present at a level of from about 0.05% to about 1.0%, preferably from about 0.2% to about 0.4%, of the compositions, together with magnesium aluminum silicate ($Al_2Mg_8Si_2$), present at a level of from about 0.1% to about 3.0%, preferably from about 0.5% to about 2.0%. of the compositions. Magnesium aluminum silicate occurs naturally in such smectic minerals as colerainite, saponite and sapphire. Refined magnesium aluminum silicates useful herein are readily available, for example as veegum, manufactured by R. T. Vanderbilt Company, Inc. Mixtures of suspending agents are also suitable for use in the compositions of this invention.

Other useful thickening agents are the cross-linked polyacrylates such as those manufactured by B. F. Goodrich and sold under the CARBOPOL® trade name.

Another optional component for use in the present compositions is an amide. The amide used in the present compositions can be any of the alkanolamides of fatty acids known for use in shampoos. These are generally mono- and diethanolamides of fatty acids having from about 8 to 24 carbon atoms. Preferred are coconut monoethanolamide, lauric diethanolamide and mixtures thereof. The amide is present at a level of from about 1% to about 10% of the compositions.

The compositions may also contain nonionic polymer material which is used at a low level to aid in dispersing particles. The material can be any of a large variety of types including cellulosic materials such as hydroxypropyl methyl cellulose, carboxymethyl cellulose, hydroxyethyl cellulose and sodium carboxymethyl cellulose as well as mixtures of these materials. Other materials include alginates, polyacrylic acids, polyethylene glycol and starches, among many others. The nonionic polymers are discussed in detail in *Industrial Gums,* edited by Roy L. Whistler, academic Press, Inc., 1973, and *Handbook of Water-Soluble Gums and Resins,* edited by Robert L. Davidson, McGraw-Hill, Inc., 1980. Both of these books in their entirety are incorporated herein by reference.

When included, the nonionic polymer is used at a level of from about 0.001% to about 0.1%, preferably from about 0.002% to about 0.05%, of the composition. Hydroxypropyl methyl cellulose is the preferred polymer.

Another suitable optional component useful in the present compositions is a nonvolatile silicone fluid.

The nonvolatile silicone fluid may be either a polyalkyl siloxane, a polyaryl siloxane, a polyalkylarly siloxane or a polyether siloxane copolymer and is present at a level of from about 0.1% to about 10.0%, preferably from about 0.5% to about 5.0%. Mixtures of these fluids may also be used and are preferred in certain executions. The dispersed silicone particles should also be insoluble in the shampoo matrix. This is the meaning of "insoluble" as used herein.

The essentially nonvolatile polyalkyl siloxane fluids that may be used include, for example, polydimethyl siloxanes with viscosities ranging from about 5 to about 600,000 centistokes at 25° C. These siloxanes are available, for example, from the General Electric Company as the VISCASIL® series and from Dow Corning as the Dow Corning 200 series.

The siloxane viscosity can be measured by means of a glass capillary viscometer as set forth in Dow Corning Corporate Test Method CTM0004, Jul. 20, 1970. Preferably the viscosity of the these siloxanes range from about 350 centistokes to about 100,000 centistokes.

The essentially nonvolatile polyether siloxane copolymer that may be used is, for example, a polypropylene oxide modified dimethylpolysiloxane (e.g., Dow Corning DC-1248), although ethylene oxide or mixtures of ethylene oxide and propylene oxide may also be used.

Suitable silicone fluids are described in U.S. Pat. No. 2,826,551, Geen; U.S. Pat. No. 3,946,500, Jun. 22, 1976, Drakoff; U.S. Pat. No. 4,364,837, Pader; and British Patent 849,433, Woolston. all of these patents are incorporated herein by reference. Also incorporated herein by reference is *Silicon Compounds,* distributed by Petrarch Systems, Inc., 1984. This reference provides a very good listing of suitable silicone materials.

Another silicone material useful is silicone gum. Silicone gums are described by Petrarch and others including U.S. Pat. No. 4,152,416, May 1, 1979, Spitzer, et al., and Noll, *Chemistry and Technology of Silicones,* New York, academic Press, 1968. Useful silicone gums are also described in General Electric Silicone Rubber Product Data Sheets SE 30, SE 33, SE 54 and SE 76. All of these references are incorporated herein by reference. "Silicone gum" materials denote high molecular weight polydiorganosiloxanes having a molecular weight of from about 200,000 to about 1,000,000. Specific examples include polydimethylsiloxane, (polydimethylsiloxane) (methylvinylsiloxane) copolymer, poly(dimethylsiloxane) (diphenyl) (methylvinylsiloxane) copolymer, and mixtures thereof. Mixtures of silicone fluids and silicone gums are also useful herein.

The shampoos herein can contain a variety of other nonessential optional components suitable for rendering such compositions more formulatable, or aesthetically and/or cosmetically acceptable. Such conventional optional ingredients are well-known to those skilled in the art and include, e.g., preservatives, such as benzyl alcohol, methyl paraben, propyl paraben, and imidazolinidyl urea; cationic surfactants, such as cetyl trimethyl ammonium chloride, lauryl trimethyl ammonium chloride, tricetyl methyl ammonium chloride, stearyldimethyl benzyl ammonium chloride, and di(partially hydrogenated tallow) dimethylammonium chloride; menthol; thickeners and viscosity modifiers, such as block polymers of ethylene oxide and propylene oxide such as PLURONIC® F88 offered by BaSa Wyandotte, sodium chloride, sodium sulfate, propylene glycol, and ethyl alcohol; pH adjusting agents, such as citric acid, succinic acid, phosphoric acid, sodium hydroxide, sodium carbonate; perfumes; dyes; and sequestering agents, such as disodium ethylenediamine tetraacetate. Such agents generally are used individually at a level of from about 0.01% to about 10%, preferably from about 0.5% to about 5.0%, of the composition.

A typical shampoo composition might comprise (percentages by weight):

(1) Alkyl aldonolactone ester 5–15%;

(2) Anionic coactive 0–10%;

(2) Amphoteric coactive 0–10%;
(4) Lauramide MEA 0–5%;
(5) Thickener 0–5%;
(6) Fragrance 0–2%;
(7) Preservative 0–1%; and
(8) Remainder water In a fifth embodiment of the invention, the alkyl aldonolactone ester surfactant of the invention may be used in a conditioner composition such as is taught and described in U.S. Pat. No. 4,913,828 to Caswell et al. which is hereby incorporated by reference.

More particularly, conditioner compositions are those containing a conditioning agent (e.g. alkylamine compounds) such as those described in U.S. Pat. No. 4,913,828.

In a sixth embodiment of the invention, the surfactant may be used in a cosmetic composition, such as is taught and is described in EP 0,371,803.

Such compositions generally comprise thickening agents, preservatives and further additions.

The composition may comprise polymer thickener in an amount sufficient to adjust the viscosity of the composition, so as to facilitate dispensing it conveniently onto the body surface.

Examples of polymer thickeners include: anionic cellulose materials, such as sodium carboxymethyl cellulose; anionic polymers such as carboxyvinyl polymers, for example, CARBOMER® 940 and 941; nonionic cellulose materials, such as methyl cellulose and hydroxypropylmethyl cellulose; cationic cellulose materials, such as POLYMER JR® 400; cationic gum materials, such as JAGUAR® C13 S; other gum materials such as gum acacia, gum tragacanth, locust bean gum, guar gum and carrageenan; proteins, such as albumin and protein hydrolysates; and clay materials, such as bentonite, hectorite, magnesium aluminum silicate, or sodium magnesium silicate.

Generally, the thickening agent may comprise from 0.05 to 5%, preferably 0.1 to 1% by weight of the composition.

The composition according to the invention can also optionally comprise a preservative to prevent microbial spoilage.

Examples of preservatives include:

(i) Chemical preservatives, such as ethanol, benzoic acid, sodium benzoate, sorbic acid, potassium sorbate, sodium propionate and the methyl, ethyl, propyl and butyl esters of p-hydroxybenzoic acid 2-bromo-2-nitropropane-1,3-diol, phenoxyethanol, dibromodicyanobutane, formalin and TRICOLSAN®. The amount of chemical preservative optionally to be incorporated in the composition according to the invention will generally be from 0.05 to 5%, preferably from 0.01 to 2% by weight, the amount chosen being sufficient to arrest microbial proliferation.

(ii) Water activity depressants, such as glycerol, propylene glycol, sorbitol, sugars and salts, for examples alkali metal halides, sulphates and carboxylates. When employing a water activity depressant, quantities sufficient should be incorporated in the composition according to the invention to reduce the water activity from 1 to <0.9, preferably to <0.85 and most preferably <0.8, the lowest of these values being that at which yeasts, molds and fungi will not proliferate.

The composition can also contain other optional adjuncts, which are conventionally employed in compositions for topical application to human skin. These adjuncts, when present, will normally form the balance of the composition.

Examples of optional adjuncts include vehicles, the selection of which will depend on the required product form of the composition. Typically, the vehicle when present, will be chosen from diluents, dispersants or carriers for the dialkyl or dialkenyl phosphate salt so as to ensure an even distribution of it when applied to the skin.

Compositions according to this invention can include water as a vehicle, usually with at least one other cosmetically-acceptable vehicle.

Vehicles other than water that can be used in compositions according to the invention can include liquids or solids as emollients, solvents, humectants, thickeners and powders. Examples of each of these types of vehicles, which can be used singly or as mixtures of one or more vehicles, are as follows:

Emollients, such as stearyl alcohol, glyceryl monolaurate, glyceryl monoricinoleate, glyceryl monostearate, propane-1,2-diol, butane-1,3 diol, docosan-1,2-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, eicosanyl alcohol, behenyl alcohol, cetyl palmitate, silicone oils such as dimethylpolysiloxane, di-n-butyl sebacate, isopropyl myristate, isopropyl palmitate, isopropyl stearate, butyl stearate, polyethylene glycol, triethylene glycol, lanolin, cocoa butter, corn oil, cotton seed oil, tallow, lard, olive oil, palm kernel oil, rapeseed oil, safflower seed oil, soybean oil, sunflower seed oil, olive oil, sesame seed oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate;

Propellants, such as trichlorofluoromethane, dichlorodifluoromethane, dichlorotetrafluoromethane, monochlorodifluoromethane, trichlorotrifluoromethane, propane, butane, isobutane, dimethyl ether, carbon dioxide, nitrous oxide;

Solvents, such as ethyl alcohol, methylene chloride, isopropanol, acetone, castor oil, ethylene glycol monoethyl ether, diethylene glycol monobutyl ether, diethylene glycol monoethyl ether, dimethyl sulphoxide, dimethyl formamide, tetrahydrofuran;

Humectants, such as glycerin, sorbitol, sodium 2-pyrrolidone-5-carboxylate, soluble collagen, dibutyl phthalate, gelatin;

Powders, such as chalk, talc, fullers earth, kaolin, starch, gums, colloidal silicon dioxide, sodium polyacrylate, tetra alkyl and/or trialkyl aryl ammonium smectites, chemically modified magnesium aluminum silicate, organically modified montmorillonite clay, hydrated aluminum silicate, fumed silica, carboxyvinyl polymer, sodium carboxymethyl cellulose, ethylene glycol monostearate.

The cosmetically acceptable vehicle, when present, will usually form from 0.01 to 99.9%, preferably from 59 to 98% by weight of the composition, and can, in the absence of other cosmetic adjuncts, form the balance of the composition.

A wide variety of conventional sunscreening agents, such as those described in U.S. Pat. No. 4,919,934 to Deckner et al. hereby incorporated by reference, may also be used in the cosmetic compositions of the invention.

Such agents include, for example, p-aminobenzoic acid, its salts and its derivatives, anthranilates, salicylates, cinnamic acid derivatives, di- and trihydroxy cinnamic acid derivatives, hydrocarbons such as diphenylbutadiene and stilbene, dibenzalacetone and benzalacetophenone, naphthasulfonates, di-hydroxy naphthloic acid and its salts, hydroxy diphenylsulfonates, coumarin derivatives, diazoles, quinine salts, quinoline derivatives, hydroxy or methoxy substituted benzophenones, uric or vilouric acid, tannic acid and its derivatives, hydroquinone, and benzophenones.

In a seventh embodiment of the invention, the surfactant may be used in a toothpaste composition such as is taught and is described in U.S. Pat. No. 4,935,227 to Duckworth, which is hereby incorporated by reference.

Such compositions generally comprise abrasive gels (e.g. calcium carbonate), oral therapeutic agents (e.g., flourine containing compound), coactives, flavoring agents, sweetening agents, humectants and binding or thickening gels.

Preferred toothpastes of this invention comprise 0 to 1.5% by weight of anionic surfactant. In more preferred products the amount of anionic surfactant is 0 to 1% by weight with most preferred amounts being 0 to 0.75% by weight.

Toothpastes of this invention may include other surfactants, especially non-ionic surfactants.

Toothpaste of the invention will also comprise the usual additional ingredients in particular humectant binder or thickening agent.

Humectants which may be used include glycerol, sorbitol syrup, polyethylene glycol, lactitol, xylitol or hydrogenated corn syrup. The total amount of humectant present will generally range from 10% to 85% by weight of the toothpaste.

Numerous binding or thickening agents have been indicated for use in toothpastes, preferred ones being sodium carboxymethylcellulose, cross-linked polyacrylates and xanthan gum. Others include natural gum binders such as gum tragacanth, gum karaya and gum arabic, Irish moss, alginates, and carrageenans. Silica thickening agents include the silica aerogels and various precipitated silicas. Mixtures of binders and thickeners may be used. The amount of binder and thickening agent included in a toothpaste is generally between 0.1 and 15% by weight.

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. A surfactant composition comprising an aldonolactone ester compound of the formula:

$$\begin{array}{cc} \text{O} & \text{O} \\ \| & \| \\ CH_2-OCR & CH_2-OCR \\ | & | \\ n(YOHC) & n(YOHC) \\ | & | \\ HC-O & \rightleftharpoons \quad HC-OH \ OH \\ | \quad | & | \quad / \\ m(YOHC)-C & m(YOHC)-C \\ \ \ \backslash\!\!\backslash & \ \ \backslash\!\!\backslash \\ \text{O} & \text{O} \\ \text{NONIONIC} & \text{ANIONIC} \end{array}$$

wherein R is a straight chain saturated alkyl radical containing 6 to 24 carbon atoms or branched alkyl or alkenyl radical containing moieties selected from the group consisting of cycloaliphatic and polyalkyloxyalkyl containing 8 to 18 carbon atoms wherein n is an integer from 0 to 3, wherein m is 2 or 3 and wherein y is selected from the group consisting of hydrogen, carbohydrate, ethoxylated carbohydrate and propoxylated carbohydrate.

2. A composition as defined in claim 1 wherein R is a substituted saturated or unsaturated radical containing 8 to 18 carbon atoms, n is 0, m is 2 or 3 and y is hydrogen.

3. A composition as defined in claim 2 wherein R is a straight chain saturated alkyl radical containing 10 to 14 carbon atoms, n is 0, m is 3, and y is hydrogen.

4. A personal product composition comprising an aldonoloctone ester as defined in claim 1.

5. A personal product composition according to claim 4 wherein the composition is a toilet bar soap.

6. A composition according to claim 5, comprising:

| Ingredients | % by Weight |
|---|---|
| $C_8$–$C_{24}$ fatty acid | 5–60% |
| said Aldonolactone ester | 1–45% |
| Alkyl or aryl sulfate or sulfonate | 0–5% |
| Coactive other than said Aldonolactone ester | 0–50% |
| Sorbitol | 0.1–10% |
| Cellulose | 0–10% |
| Sequestering agent | 0.1–0.5% |
| Water and minors | Balance to 100% |

7. A personal product composition according to claim 4, wherein the composition is a facial/body cleanser.

8. A personal product composition according to claim 4 wherein the composition is a shower gel.

9. A personal product composition according to claim 4 wherein the composition is a shaving cream.

10. A composition according to claim 1 comprising the following:

| Ingredient | % by Weight |
|---|---|
| $C_8C_{24}$ fatty acid salt | 1–45% |
| said Aldonolactone ester | 10–75% |
| Alkyl or aryl sulfate or sulfonate | 0–20% |
| Cocamidobetaine | 1–15% |
| Sorbitol | 0.1–15% |
| fatty alcohol | 0.5–5% |
| Water soluble polymer | 0–10% |
| Thickener | 0–15% |
| Quaternized cellulose | 0–0.5% |
| Citrate | 0.1–0.4% |
| Water and minors | Balance to 100% |

11. A composition according to claim 4, wherein the composition is a bar or body shampoo.

12. A composition according to claim 11 comprising:

| | | |
|---|---|---|
| (1) said aldonolactone ester | 5–15%; | |
| (2) Anionic coactive, other than said aldonolactone ester | 0–10%; | |
| (3) Amphoteric coactive, other than said aldonolactone ester | 0–10%; | |
| (4) Lauramide MEA | 0–5%; | |
| (5) Thickener | 0–5%; | |
| (6) Fragrance | 0–2%; | |
| (7) Preservative | 0–1%; and | |
| (8) Remainder water | | |

13. A composition according to claim 4, wherein the composition is a conditioner composition.

14. A composition according to claim 4, wherein the composition is a cosmetic composition.

15. A composition according to claim 1, wherein the composition is a liquid detergent.

16. A composition according to claim 1, wherein the composition is a powdered detergent.

17. A liquid detergent composition according to claim 15 comprising:

(1) 1–50% of said aldonolactone ester (2) 5–70% detergent active other than said aldonolactone ester;

(3) 0–20% builder;

(4) 0–40% electrolyte;

(5) 0.01–5% enzyme;

(6) 0.1–15% enzyme stabilizer;
(7) 0–20% phase regulant; and
(8) remainder water and minors.

18. A powdered detergent composition according to claim 16, comprising:
    (1) 1–40% of said aldonolactone ester;
    (2) 5–40% additional surface active agent other than said aldonolactone ester;
    (3) 0–40% builder;
    (4) 0–30% buffer salt;
    (5) 0–30% sulfate;
    (6) 0–20% bleach system;
    (7) 0–4% enzyme;
    (8) remainder water and minors.

19. A composition according to claim 1 wherein the composition is a fabric softener.

20. A surfactant composition comprising an aldonolactone ester compound of the formula:

$$\begin{array}{cc}
\underset{\text{NONIONIC}}{\begin{array}{c}CH_2-OCR \\ | \\ n(YOHC) \\ | \\ HC-O \\ | \\ m(YOHC)-C \\ \phantom{m(YOHC)-}\diagdown O\end{array}} & \underset{\text{ANIONIC}}{\begin{array}{c}CH_2-OCR \\ | \\ n(YOHC) \\ | \\ HC-OH\phantom{O}OH \\ | \phantom{HC-OH}/ \\ m(YOHC)-C \\ \phantom{m(YOHC)-}\diagdown O\end{array}}
\end{array}$$

wherein R is a straight chain saturated alkyl radical containing 8 to 18 carbon atoms or branched alkyl or alkenyl radical containing moieties selected from the group consisting of cycloaliphatic and polyalkyloxyalkyl containing 8 to 18 carbon atoms wherein n is an integer from 0 to 3, wherein m is 2 or 3 and wherein y is a carbohydrate selected from the group consisting of mono-, di- and oligosaccharides.

21. A composition as defined in claim 20 wherein R is a substituted saturated or unsaturated radical containing 8 to 18 carbon atoms, n is 0, m is 2 or 3 and y is hydrogen.

22. A composition as defined in claim 21 wherein R is a straight chain saturated alkyl radical containing 10 to 14 carbon atoms, n is 0, m is 3, and y is hydrogen.

23. A personal product composition comprising an aldonoloctone ester as defined in claim 20.

24. A personal product composition according to claim 23 wherein the composition is a toilet bar soap.

25. A composition according to claim 24, comprising:

| Ingredients | % by Weight |
| --- | --- |
| $C_8$–$C_{24}$ fatty acid | 5–60% |
| said Aldonolactone ester | 1–45% |
| Alkyl or aryl sulfate or sulfonate | 0–5% |
| Coactive other than said Aldonolactone ester | 0–50% |
| Sorbitol | 0.1–10% |
| Cellulose | 0–10% |
| Sequestering agent | 0.1–0.5% |
| Water and minors | Balance to 100% |

26. A personal product composition according to claim 23, wherein the composition is a facial/body cleanser.

27. A personal product composition according to claim 23 wherein the composition is a shower gel.

28. A personal product composition according to claim 23 wherein the composition is a shaving cream.

29. A composition according to claim 20 comprising the following:

| Ingredient | % by Weight |
| --- | --- |
| $C_8C_{24}$ fatty acid salt | 1–45% |
| said Aldonolactone ester | 10–75% |
| Alkyl or aryl sulfate or sulfonate | 0–20% |
| Cocamidobetaine | 1–15% |
| Sorbitol | 0.1–15% |
| fatty alcohol | 0.5–5% |
| Water soluble polymer | 0–10% |
| Thickener | 0–15% |
| Quaternized cellulose | 0–0.5% |
| Citrate | 0.1–0.4% |
| Water and minors | Balance to 100% |

30. A composition according to claim 23, wherein the composition is a bar or body shampoo.

31. A composition according to claim 30 comprising:

| | |
| --- | --- |
| (1) said aldonolactone ester | 5–15%; |
| (2) Anionic coactive, other than said alconolactone ester | 0–10%; |
| (3) Amphoteric coactive, other than said alconolactone ester | 0–10%; |
| (4) Lauramide MEA | 0–5%; |
| (5) Thickener | 0–5%; |
| (6) Fragrance | 0–2%; |
| (7) Preservative | 0–1%; and |
| (8) Remainder water | |

32. A composition according to claim 23, wherein the composition is a conditioner composition.

33. A composition according to claim 23, wherein the composition is a cosmetic composition.

34. A composition according to claim 20 wherein the composition is a liquid detergent.

35. A composition according to claim 20 wherein the composition is a powdered detergent.

36. A liquid detergent composition according to claim 34 comprising:
    (1) 1–50% of said alconolactone ester;
    (2) 5–70% detergent active other than said aldonolactone ester;
    (3) 0–20% builder;
    (4) 0–40% electrolyte;
    (5) 0.01–5% enzyme;
    (6) 0.1–15% enzyme stabilizer;
    (7) 0–20% phase regulant; and
    (8) remainder water and minors.

37. A powdered detergent composition according to claim 35 comprising:
    (1) 1–40% of said aldonolactone ester;
    (2) 5–40% additional surface active agent other than said aldonolactone ester;
    (3) 0–40% builder;
    (4) 0–30% buffer salt;
    (5) 0–30% sulfate;
    (6) 0–20% bleach system;
    (7) 0–4% enzyme;
    (8) remainder water and minors.

38. A composition according to claim 20 wherein the composition is a fabric softener.

39. A surfactant composition comprising an aldonolactone ester compound of the formula:

$$\underset{\text{NONIONIC}}{\overset{\overset{O}{\underset{\|}{CH_2-OCR}}}{\underset{\underset{O}{m(YOHC)-C\diagdown\diagup}}{\underset{HC-O}{n(YOHC)}}}} \rightleftharpoons \underset{\text{ANIONIC}}{\overset{\overset{O}{\underset{\|}{CH_2-OCR}}}{\underset{\underset{O}{m(YOHC)-C\diagdown\diagup}}{\underset{HC-OH\ OH}{n(YOHC)}}}}$$

wherein R is a straight chain saturated or unsaturated alkyl radical containing 8 to carbon atoms, wherein n is 0, wherein m is 3 and wherein y is hydrogen.

40. A surfactant composition as defined in claim 39 wherein said aldonolactone ester is selected from the group consisting of:

6-O-Decyl-δ-D-Gluconolactone Ester

6-O-Dodecyl-δ-D-Gluconolactone Ester

6-O-Tetradecyl-δ-D-Gluconolactone Ester

6-O-Decanoyl-D-Gluconic Acid

6-O-Dodecanoyl-D-Gluconic Acid; and

6-O-Tetradecanoyl-D-Gluconic Acid.

41. A surfactant composition as defined in claim 39 wherein aldonolactone ester compound has the formula:

[Structural formula showing gluconolactone ester ⇌ gluconic acid ester with +H₂O/−H₂O]

wherein R is a straight chain saturated or unsaturated alkyl radical containing 10 to 14 carbon atoms.

42. A personal product composition comprising an aldonolactone ester as defined in claim 39.

43. A personal product composition according to claim 42 wherein the composition is a toilet bar soap.

44. A composition according to claim 43, comprising:

| Ingredients | % by Weight |
| --- | --- |
| $C_8$–$C_{24}$ fatty acid | 5–60% |
| said Aldonolactone ester | 1–45% |
| Alkyl or aryl sulfate or sulfonate | 0–5% |
| Coactive other than said Aldonolactone ester | 0–50% |
| Sorbitol | 0.1–10% |
| Cellulose | 0–10% |
| Sequestering agent | 0.1–0.5% |
| Water and minors | Balance to 100% |

45. A personal product composition according to claim 42, wherein the composition is a facial/body cleanser.

46. A personal product composition according to claim 42 wherein the composition is a shower gel.

47. A personal product composition according to claim 42 wherein the composition is a shaving cream.

48. A composition according to claim 39 comprising the following:

| Ingredient | % by Weight |
| --- | --- |
| $C_8C_{24}$ fatty acid salt | 1–45% |
| said Aldonolactone ester | 10–75% |
| Alkyl or aryl sulfate or sulfonate | 0–20% |
| Cocamidobetaine | 1–15% |
| Sorbitol | 0.1–15% |
| fatty alcohol | 0.5–5% |
| Water soluble polymer | 0–10% |
| Thickener | 0–15% |
| Quaternized cellulose | 0–0.5% |
| Citrate | 0.1–0.4% |
| Water and minors | Balance to 100% |

49. A composition according to claim 42, wherein the composition is a bar or body shampoo.

50. A composition according to claim 49 comprising:

| | |
| --- | --- |
| (1) said aldonolactone ester | 5–15%; |
| (2) Anionic coactive, other than said aldonolactone ester | 0–10%; |
| (3) Amphoteric coactive, other than said aldonolactone ester | 0–10%; |
| (4) Lauramide MEA | 0–5%; |
| (5) Thickener | 0–5%; |
| (6) Fragrance | 0–2%; |
| (7) Preservative | 0–1%; and |
| (8) Remainder water. | |

51. A composition according to claim 42, wherein the composition is a conditioner composition.

52. A composition according to claim 42, wherein the composition is a cosmetic composition.

53. A composition according to claim 39, wherein the composition is a liquid detergent.

54. A composition according to claim 39, wherein the composition is a powdered detergent.

55. A liquid detergent composition according to claim 53 comprising:

(1) 1–50% of said aldonolactone ester (2) 5–70% detergent active other than said aldonolactone ester;

(3) 0–20% builder;

(4) 0–40% electrolyte;

(5) 0.01–5% enzyme;

(6) 0.1–15% enzyme stabilizer;

(7) 0–20% phase regulant; and (8) remainder water and minors.

56. A powdered detergent composition according to claim 54 comprising:

(1) 1–40% of said aldonolactone ester;

(2) 5–40% additional surface active agent other than said aldonolactone ester;

(3) 0–40% builder;

(4) 0–30% buffer salt;

(5) 0–30% sulfate;

(6) 0–20% bleach system;

(7) 0–4% enzyme;

(8) remainder water and minors.

57. A composition according to claim 39 wherein the composition is a fabric softener.

58. An enzymatic process for preparing aldonolactone ester compounds of the formula:

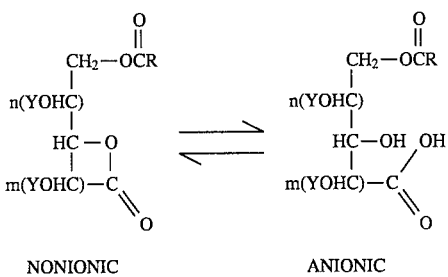

NONIONIC       ANIONIC wherein R is a straight chain saturated or unsaturated alkyl radical containing 8 to 18 carbon atoms wherein n is an integer from 0 to 2, wherein m is 2 or 3 and wherein y is selected from the group consisting of hydrogen or monosaccharide comprising:

dissolving an aldonolactone and a fatty acid ester in an organic solvent to form an aldonolactone fatty ester acid solution in a molar amount of about 1 to about 5 moles of said aldonolactone to said fatty acid ester;

adding a catalytic amount of an enzyme to said solution; followed by agitating and heating said solution at a temperature of about 30° C. to about 100° C.

59. A process as defined in claim 58 wherein said fatty acid ester is selected from the group consisting of methyl alkanoates, ethyl alkanoates, propyl alkanoates, n-butyl alkanoates, isopropenyl alkanoates, oximine alkanoates, vinyl alkanoates, alkyl anhydrides glycerides and trihaloalkyl alkanoates.

60. A process as defined in claim 58 where said aldonolactone is selected from the group consisting of glucoheptonolactone; glucooctonolactone; glyceromannoheptonolactone; gluconolactone; lactobionolactone; maltobionolactone; erythronolactone and xylonolactone.

61. A process as defined in claim 58 wherein said enzyme is a lipase isolated from a microorganism selected from a group consisting of humicula, pseudomonas, candida, chromobacterium, mucor, rhizopus and aspergillus.

62. A process as defined in claim 58 wherein said enzyme is porcine pancreatic lipsase.

63. A process as defined in claim 58 wherein n is an integer from 0 to 1.

64. A process as defined in claim 58 wherein n is an integer from 0 to 1 and Y is hydrogen.

* * * * *